United States Patent [19]

Costa

[11] 4,361,402

[45] Nov. 30, 1982

[54] APPARATUS FOR DETERMINING THE REFRACTIVE-INDEX PROFILE OF OPTICAL FIBERS

[75] Inventor: Bruno Costa, Turin, Italy

[73] Assignee: Cselt - Centro Studi E Laboratori Telecomunicazioni S.p.A., Turin, Italy

[21] Appl. No.: 174,694

[22] Filed: Aug. 1, 1980

[30] Foreign Application Priority Data

Aug. 2, 1979 [IT] Italy .............................. 68600 A/79

[51] Int. Cl.³ ............................................ G01N 21/00
[52] U.S. Cl. .................................. 356/73.1; 356/128; 350/15
[58] Field of Search ...................... 356/73.1, 128, 445, 356/364, 365, 369; 350/15

[56] References Cited

U.S. PATENT DOCUMENTS 2,318,705  5/1943  Morgan .................................. 350/15
4,212,537  7/1980  Golob et al. ......................... 356/73.1

OTHER PUBLICATIONS

"Measuring Method for the Refractive Index Profile of Optical Glass Fibers, Eickhoff et al., Optics & Quantum Electronics", 7, (1975), 109–113.
"Refractive Index Profile of a Graded Index Fiber: Measurement by Reflection Method, Ikeda et al., Applied Optics", vol. 14, #4, Apr. 1975, pp. 814–815.
"Measurements of the Refractive Index Profile in Optical Fibers: Comparison between Different Techniques", Costa et al., (Second European Conference of Optical-Fiber Communications, undated).

Primary Examiner—Vincent P. McGraw
Attorney, Agent, or Firm—Karl F. Ross

[57] ABSTRACT

Light from a laser, converted into pulses by a chopper, is trained upon an end of an optical fiber—whose refractive-index profile is to be determined—through a first polarizer, a beam splitter, a focusing objective and a 90° phase shifter, the space between the objective and the fiber end being occupied by a fluid whose refractive index is close to that of the fiber. Light reflected from the fiber end, having passed twice through the phase shifter, has a plane of polarization orthogonal to that of the incident light and is passed by a second polarizer, to which it is directed by the beam splitter, onto a photodiode feeding a calculator that also receives a reference signal from another photodiode to which part of the polarized laser pulses are directly reflected by the beam splitter. Spurious reflections from the objective surface, which do not pass through the phase shifter, retain the original polarization and are rejected by the second polarizer.

4 Claims, 1 Drawing Figure

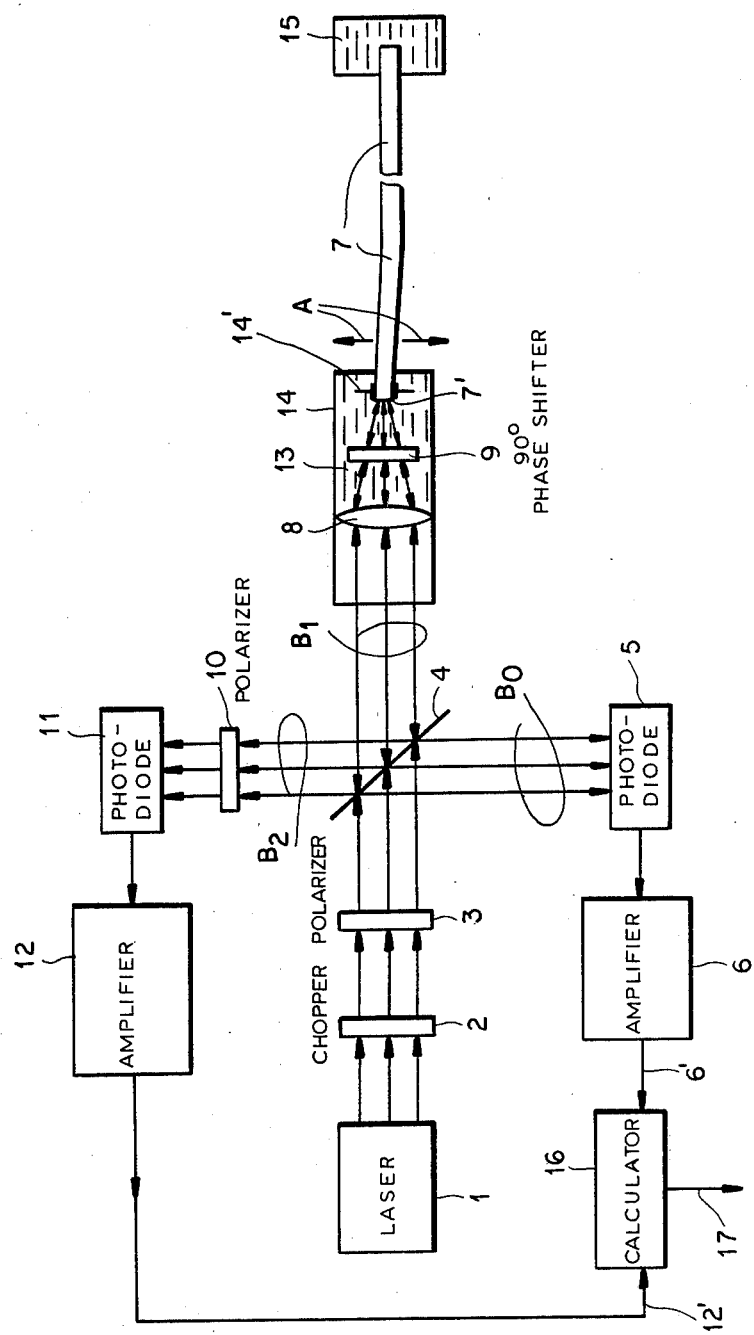

APPARATUS FOR DETERMINING THE REFRACTIVE-INDEX PROFILE OF OPTICAL FIBERS

FIELD OF THE INVENTION

My present invention relates to an apparatus for determining the refractive-index profile of optical fibers.

BACKGROUND OF THE INVENTION

The refractive index of an optical fiber is known to vary, within relatively narrow limits, gradually or in steps throughout its cross-section as a function of radius. A knowledge of this variation, known as the index profile, is important for a determination of some of the basic characteristics of a fiber such as its light-gathering efficiency, its light-guiding properties and its bandwidth.

Several techniques have already been developed for this purpose. Among them is the reflection method according to which a light beam is focused upon a substantially punctiform area (usually on the order of 1$\mu$ in diameter) of a fiber end by an optical objective through which reflected luminous energy is passed by suitable light-guiding means such as a beam splitter to a photodetector feeding an evaluator. As the projected light spot is displaced along a diametrical line of the fiber end confronting the objective, the evaluator calculates the refractive index from the reflected energy and plots it for different distances from the fiber axis; this calculation can be carried out with the aid of a reference value derived, advantageously via the aforementioned beam splitter, from the output of the light source.

Index-determining systems of this type have been described in an article by W. Eickhoff and E. Weidel entitled "Measuring Method for the Refractive Index Profile of Optical Glass Fibres", published March 1975 in *Optical and Quantum Electronics,* Vol. 7, No. 2, and in an article by Masahiro Ikeda, Mitsuhiro Tateda and Haruo Yoshikiyo entitled "Refractive Index Profile of a Graded Index Fiber: Measurement by a Reflection Method", published April 1975 in *Applied Optics,* Vol. 14, No. 4. Both these articles are referred to in a paper by B. Sordo and me entitled "Measurements of the Refractive Index Profile in Optical Fibres: Comparison between Different Techniques" which was presented at the Second European Conference on Optical-Fiber Communication, 20 to 30 September 1976, Paris; this paper proposes the use of a fluid (oil), of a refractive index closely approaching that of the fiber to be tested, in the space between the focusing objective and the confronting fiber end.

Even with the improvement last described, such an apparatus is not free from drawbacks. More particularly, spurious reflections at the objective itself tend to superimpose themselves upon the light reflected at the fiber end so as to falsify the evaluation results. These spurious reflections, despite their low absolute power, may have a significant influence upon the measured values since the refractive index varying along a continuous (e.g. parabolic) curve may change from one area of illumination to the next by increments on the order of 0.001 whose detection requires the sensing of differences in reflected energy amounting to a fraction of one percent. Thus, a system using an index-matching fluid as discussed above will give rise to reflected energy at the fiber end amounting to about $10^{-4}$ times the incident energy which would be overshadowed by the spurious reflections at the objective surfaces; while this problem could be alleviated by the use of lenses with antireflection coatings, the latter would have to be specifically designed for the luminous wavelength employed and would be difficult to apply to an existing, commercially available objective. Moreover, with coherent light emitted by a gas laser serving as the source, the spurious reflected rays will interfere with the incident rays and give rise to a time-varying power distribution resulting in an unstable output signal.

OBJECT OF THE INVENTION

The object of my present invention, therefore, is to provide an improved apparatus for determining the index profile of an optical fiber by the reflection method which obviates the aforedescribed drawbacks and is readily adaptable to different wavelengths.

SUMMARY OF THE INVENTION

I realize this object, in accordance with my present invention, by interposing a $\pi/2$ phase shifter between the focusing objective and the confronting fiber end illuminated thereby so that plane-polarized light reflected by that fiber end is intercepted by the associated light-guiding means (e.g. a beam splitter) after two traverses of that phase shifter and has a plane of polarization orthogonal to that of spurious light rays reflected by the objective since these latter light rays do not pass through the phase shifter. A polarizer inserted between the light-guiding means and the evaluation means passes only the light reflected at the fiber end, to the exclusion of the spurious light rays.

The 90° phase shifter, which preferably is a $\lambda/4$ plate, can be readily exchanged when it is desired to use light of a different wavelength.

BRIEF DESCRIPTION OF THE DRAWING

The above and other features of my invention will now be described in detail with reference to the accompanying drawing the sole FIGURE of which schematically shows a representative embodiment.

SPECIFIC DESCRIPTION

As shown in the drawing, a laser 1 serving as a source of coherent light illuminates a beam splitter 4 by way of a chopper 2 and a polarizer 3; the latter, of course, may be omitted if the light entering the chopper 2 is already linearly polarized. The beam splitter 4 divides the pulsating light into a reflected reference beam $B_O$, directed to a photodiode 5, and a transmitted illuminating beam $B_1$ impinging upon an objective 8 in a housing 14 provided with a support 14' which holds an extremity of an optical fiber 7 to be tested. The space between objective 8 and the confronting end 7' of fiber 7 is filled with a fluid 13, such as oil, whose refractive index substantially matches that of the fiber. The opposite end of fiber 7 is immersed in similar fluid in a container 15 with nonreflecting inner wall surfaces.

Objective 8 focuses the incident beam $B_1$ upon a small spot on fiber end 7' from which luminous energy is reflected via the same path, and thus by way of objective 8, toward beam splitter 4. Part of the returning light, which includes spurious rays reflected by lens surfaces of the objective, is redirected as a measuring beam $B_2$ to an evaluator which includes, besides the aforementioned photodiode 5, a second photodiode 11 and a calculator 16. Photodiodes 5 and 11 work by way of respective amplifiers 6 and 12 into respective inputs 6' and 12' of calculator 16 whose output 17 carries a signal representing the refractive index of fiber 7 at the spot of end 7' illuminated by the focused beam $B_1$. Calculator 16 operates according to the well-known Fresnel formula $$R = \left( \frac{n_o - n_r}{n_o + n_r} \right)^2$$

where R is the reflected energy and $n_r$, $n_o$ respectively represent the refractive indices of the fiber 7 and the surrounding medium 13. Support 14' and objective 8 are relatively displaced, in steps synchronized with the operation of chopper 2, in a plane perpendicular to the objective axis as indicated by arrows A. The system so far described is conventional and corresponds essentially to the one discussed in the above-identified paper by B. Sordo and me.

In accordance with my present invention, and for the purpose of eliminating the influence of spurious reflections at objective 8, I insert between that objective and the fiber end 7' a 90° (or $\pi/2$) phase shifter 9 in the form of a quarter-wavelength plate. The light of incident beam $B_1$, polarized in one plane, is converted by this phase shifter to circular polarization and is reconverted, after reflection, to linear polarization but in a plane orthogonal to the first one. Since the light reflected at objective 8 undergoes no such double conversion, the desired reflections from the fiber end and the spurious reflections from the objective have polarization planes perpendicular to each other as they arrive at a second polarizer (or analyser) 10 which allows only the former to pass toward photodiode 11.

In order to avoid interferences between the incident and the reflected light rays in the region where their polarization is the same, i.e. between plate 13 and fiber end 7', I prefer to design the fiber holder 14' in such a way that the plane of the fiber end includes an angle slightly smaller than 90° with the objective axis; the latter, therefore, is inclined to the fiber axis as seen in the drawing.

The optical components 3, 4 and 10 may be designed as Glan-Thompson prisms.

I claim:

1. In an apparatus for determining the refractive-index profile of an optical fiber comprising a source of linearly polarized coherent incident light, an optical objective in the path of said incident light for focusing same on a substantially punctiform area of a confronting end of said fiber, light-guiding means for intercepting light reflected from the confronting fiber end through said objective, fiber-engaging means displaceable relatively to said objective in a plane perpendicular to the optical axis thereof, and evaluation means positioned to receive the reflected light intercepted by said light-guiding means, the combination therewith of a $\pi/2$ phase shifter inserted between said objective and said fiber end, whereby light reflected by said fiber end and intercepted by said light-guiding means after two traverses of said phase shifter has a plane of polarization orthogonal to the plane of polarization of spurious light rays reflected directly by said objective toward said light-guiding means, and a polarizer inserted between said light-guiding means and said evaluation means for passing only the light reflected by said fiber end to the exclusion of said spurious light rays, said fiber-engaging means holding said fiber end inclined at slightly less than 90° to said optical axis for avoiding interferences between the incident and the reflected coherent light.

2. The combination defined in claim 1 wherein said phase shifter is a $\lambda/4$ plate.

3. The combination defined in claim 1 or 2 wherein said phase shifter is immersed in a fluid whose refractive index substantially matches that of said fiber and which occupies the space between said objective and said fiber end.

4. The combination defined in claim 3 wherein said objective, said phase shifter and said fluid are disposed in a container provided with said fiber-engaging means.

* * * * *